(12) United States Patent
Kwok et al.

(10) Patent No.: US 7,525,663 B2
(45) Date of Patent: Apr. 28, 2009

(54) METHOD AND APPARATUS FOR HUMIDIFICATION OF BREATHABLE GAS BY CONDENSATION AND/OR DEHUMIDIFICATION

(75) Inventors: Philip Rodney Kwok, Chatswood (AU); Donald Darkin, Dural (AU)

(73) Assignee: Resmed Limited, Bella Vista, New South Wales (AU)

( * ) Notice: Subject to any disclaimer, the term of this patent is extended or adjusted under 35 U.S.C. 154(b) by 530 days.

(21) Appl. No.: 11/207,007

(22) Filed: Aug. 19, 2005

(65) Prior Publication Data

US 2006/0037613 A1 Feb. 23, 2006

Related U.S. Application Data

(60) Provisional application No. 60/602,872, filed on Aug. 20, 2004.

(51) Int. Cl.
*G01N 21/00* (2006.01)
(52) U.S. Cl. .................... 356/436; 128/203.27
(58) Field of Classification Search ......... 356/432–440, 356/445; 374/28; 250/227.25, 221, 573, 250/574; 128/203.27, 203.26, 203.16
See application file for complete search history.

(56) References Cited

U.S. PATENT DOCUMENTS

| | | | | |
|---|---|---|---|---|
| 4,701,052 A * | 10/1987 | Schoen, Jr. | .................. | 356/369 |
| 5,313,072 A * | 5/1994 | Vachss | ..................... | 250/573 |
| 5,703,568 A * | 12/1997 | Hegyi | ......................... | 340/602 |
| 5,809,826 A * | 9/1998 | Baker, Jr. | ....................... | 73/75 |
| 6,084,519 A * | 7/2000 | Coulling et al. | ............. | 340/602 |
| 6,118,383 A * | 9/2000 | Hegyi | ......................... | 340/602 |
| 6,313,454 B1* | 11/2001 | Bos et al. | ................. | 250/208.1 |
| 7,259,367 B2* | 8/2007 | Reime | ................... | 250/227.25 |
| 2007/0147467 A1* | 6/2007 | Arnold et al. | ................. | 374/28 |

\* cited by examiner

*Primary Examiner*—Hoa Q Pham
(74) *Attorney, Agent, or Firm*—Nixon & Vanderhye P.C.

(57) ABSTRACT

A method and apparatus for humidifying breathable gas provided to a user includes providing a breathable gas, producing moisture or water derived from ambient environmental surroundings, e.g., via condensation and/or dehumidified air, and directing the breathable gas along an air flow path. The air flow path optionally includes access to at least a portion of the moisture or water for increased humidification of the breathable gas, for delivery to the user.

19 Claims, 8 Drawing Sheets

METHOD AND APPARATUS FOR HUMIDIFICATION OF BREATHABLE GAS BY CONDENSATION AND/OR DEHUMIDIFICATION

CROSS-REFERENCE TO APPLICATION

This application claims the benefit of U.S. Provisional Application Ser. No. 60/602,872, filed Aug. 20, 2004, incorporated herein by reference in its entirety.

STATEMENT REGARDING FEDERALLY SPONSORED RESEARCH OR DEVELOPMENT

None.

BACKGROUND OF THE INVENTION

Humidifiers are useful to treat a number of ailments that may include nasal dryness and also prevent Rhinitis (inflammation of the nasal mucous membrane). These ailments can be caused by the introduction of relatively dry and/or cold breathing gas (e.g. air) to a patient's airways.

Humidifiers benefit the patient twofold. They add warmth to the breathing gases, which improves patient breathing comfort and also adds moisture (e.g. water) to the breathing air to reduce dryness and irritation. Both aspects are especially beneficial during cooler ambient environmental conditions such as during cooler seasons (winter).

In the treatment of a patient using ventilation means, the humidification standard is in the form of an electrical heater that warms a body of water which then evaporates the liquid into a vapor or gas that is subsequently introduced to the ventilator's air supply and delivered to the patient airways.

Other types of humidifiers exist in ventilation and may include non-heated systems. These may be known as "Passive" or "Passover" humidifiers in the art, however these devices provide limited benefit in efficiency and moisture delivery to the patient airways. Furthermore, there is no warmth being added to the breathing air, which may be irritating should the breathing gas be relatively cool.

There are also air 'wick' systems that pass water through moist surfaces or membranes to allow the air to pick up moisture. The moist surfaces generally draw water from a water reservoir through a capillary action. As the air passes over the moist surfaces, moisture is picked up and the breathing gas (air) is delivered to the patient with higher humidity levels.

Humidifiers currently manufactured for patient ventilation, such as Continuous Positive Airway Pressure (CPAP) used to treat Obstructive Sleep Apnea (OSA), have substantially large water reservoirs (400-600 ml of water capacity). These reservoirs are not user friendly as they need to be filled prior to use, they need to be emptied and cleaned between use, and they are a source of infection as bacteria can accumulate and be difficult to clean effectively.

Furthermore a patient needs to carry the reservoir to a water source and back to the bedroom after filling, prior to each treatment session. This requires more effort and inconvenience on the user's part.

Current humidification systems aim to generate efficient and high levels of humidification whilst reducing condensation in the air delivery path and mask interface. There are numerous systems that have feedback and sensor systems to maximize humidification of the breathing gas or vary humidification in conjunction with changes in conditions, e.g. ambient temperature, airflow etc.

Accordingly, a need has developed in the art to address one or more problems or shortcomings associated with prior art humidifiers.

BRIEF SUMMARY OF THE INVENTION

One aspect of the invention is to reduce the size of current technology, e.g., by substantially eliminating the water (or fluid) reservoir, and/or improving ease of use by eliminating the need to fill, empty remains of and/or clean the reservoir.

Another aspect of the invention is to provide a blower with a self-initiating and/or replenishing form of humidification.

These and other aspects will be described in or apparent from the following detailed description.

DETAILED DESCRIPTION OF PREFERRED EMBODIMENTS

One embodiment of the invention basically draws its water or moisture for humidification from the environment (air) surrounding the device.

The atmosphere that humans breathe generally contains some level of moisture or humidity in it. The apparatus described herein may use one or more of the techniques described below to extract this moisture or water from the air for subsequent use or processing prior to its final delivery to a patient's airways, preferably as a humidified breathing gas (above ambient humidity).

In another embodiment, moisture from the atmosphere is condensed onto a cooling medium that is in contact with ambient air. One way to create condensation is to cool the collection surface or surfaces below that of the adjacent ambient air (exposed to the collection surface) below the air's Dew Point. Water droplets then condense from the air and onto the collection surface.

The Dew Point is the temperature at which air must be cooled in order to reach saturation, assuming the air temperature and moisture content are constant. This saturation results in the liquid (water) condensing from the gas (water vapor).

Another embodiment relates to dehumidifying the ambient air, collecting the water as a liquid and reprocessing this water to increase the moisture content of the breathable gas.

The dehumidified ambient air may also be beneficial in households with excessive moisture in the room environment, which has benefits of reducing mold and possibly allergens that may cause asthma attacks, etc.

The chilled surface in contact with the ambient air does not need to be the actual cooling component of the mechanism. The cooled surface may also be created remotely like chillers used in large building cooling systems. There is a cooling center that subsequently 'pipes'the chilled fluid to where it is required.

Dew Point may also be changed by modifying the moisture content of ambient air, for example, using a room humidifier and/or modifying the air temperature.

Cooling may be achieved with several forms of technology from heat pumps to cold storage devices.

Peltier Heat Pump Methods

Figures 1, 2:
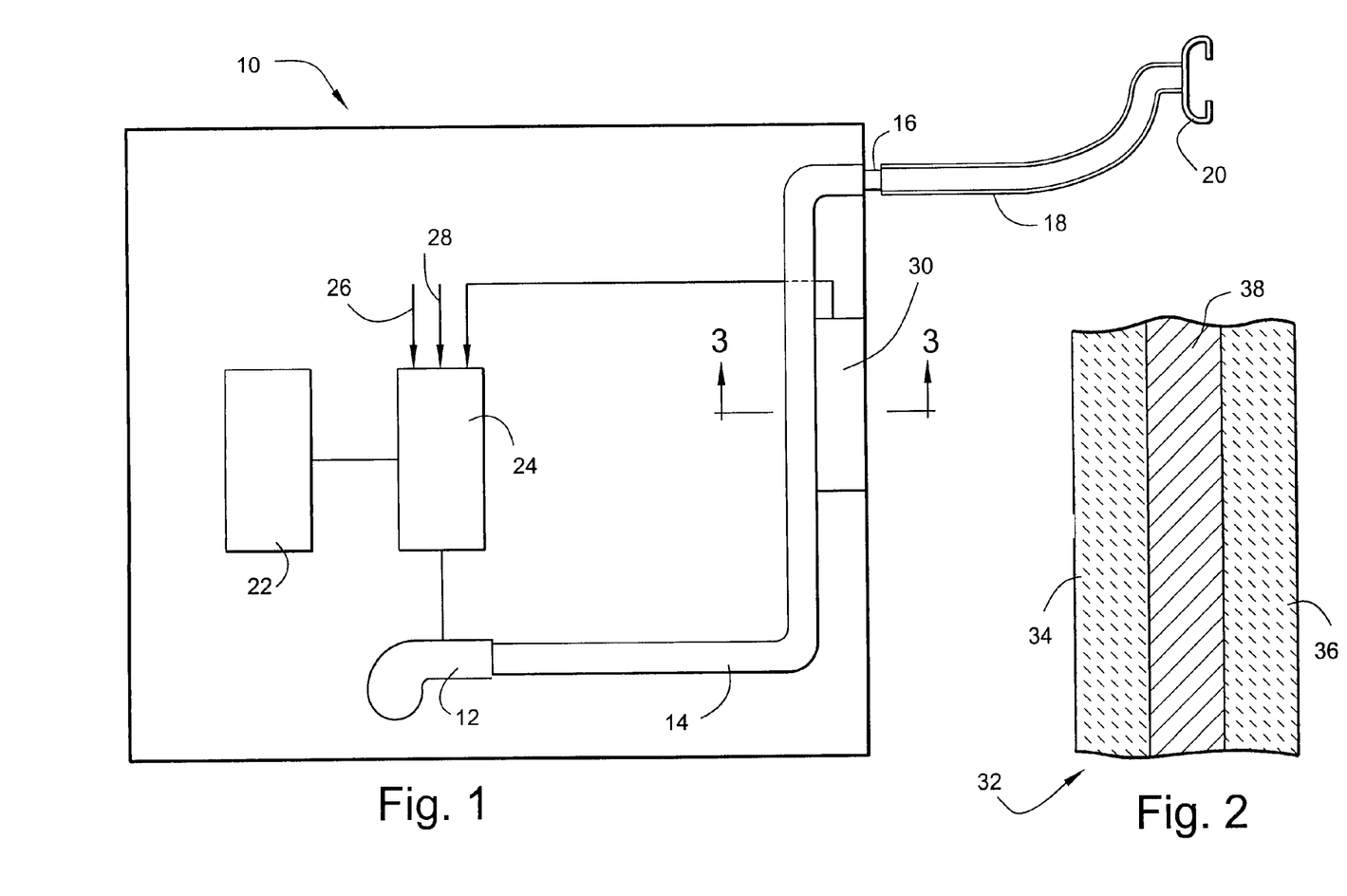
FIG. 1 is a schematic view of a blower according to an embodiment of the present invention.
FIG. 2 is a schematic explanatory view of a Peltier plate that can be used on the blower of FIG. 1.

FIG. 1 is a schematic diagram of a blower 10 according to an embodiment of the present invention. Blower 10 includes a blower motor 12 that includes an inlet for receiving atmospheric gas, e.g., air. Blower motor 12 pressurizes the breathable gas to the desired level, e.g., between about 4-20 cm $H_2O$, for delivery to an air flow path, including an internal tube 14 within the blower 10. Internal tube 14 delivers the pressurized breathable gas to an outlet 16 provided on an exterior of the blower casing. An air delivery conduit 18, also forming part of the air flow path, is provided to the outlet 16, for the delivery of pressurized breathable gas to a patient interface, such as a mask 20. The breathable gas is transferred from the air flow path to the user's airways.

Blower includes a control panel 22, which preferably includes a display. Control panel 22 is in communication with a controller 24 to control the operation of blower 10. Blower motor 12 is also connected to controller 24. In addition, controller includes a plurality of inputs 26, 28, for example, to receive signals from various sensors or transducers typically provided as part of blower 10. In general, blowers are commercially available from ResMed, Inc.

Blower 10 includes a humidification unit 30 according to a first embodiment of the present invention. Generally speaking, humidification unit 30 has the function of producing moisture or water from ambient environmental surroundings. This can help eliminate the need for a bulky humidifier unit as is used in the prior art, i.e., the size of the humidifier can be reduced or the need for a stand-alone humidifier that requires water (re-)filling can be virtually eliminated. Of course, the humidification unit can be embodied as an accessory or after market device. In addition, the humidification unit can be used to (self-)replenish the humidity level of the breathable gas. For example, the blower could be provided with an initial amount (e.g., 100-200mL) of water, and the humidification unit can produce its own moisture or water to maintain the desired humidification level, even if the initial water has been depleted. In this embodiment, humidification unit 30 includes a Peltier plate 32 as schematically shown in FIG. 2. Humidification unit 30 is in communication with controller 24.

Peltier plate 32 is similar to Peltier plates used in solid-state heat pumps. In one example of Peltier technology, two insulation layers, e.g., thin ceramic layers 34, 36, sandwich a metal layer, e.g., a Bismuth Telluride cube layer 38. As electric current is applied, heat is moved from one side of the plate to the other; therefore one side becomes cold (and produces moisture or water) whilst the other side becomes hot. Any other form of thermoelectric heat pump may be used.

Figure 3:
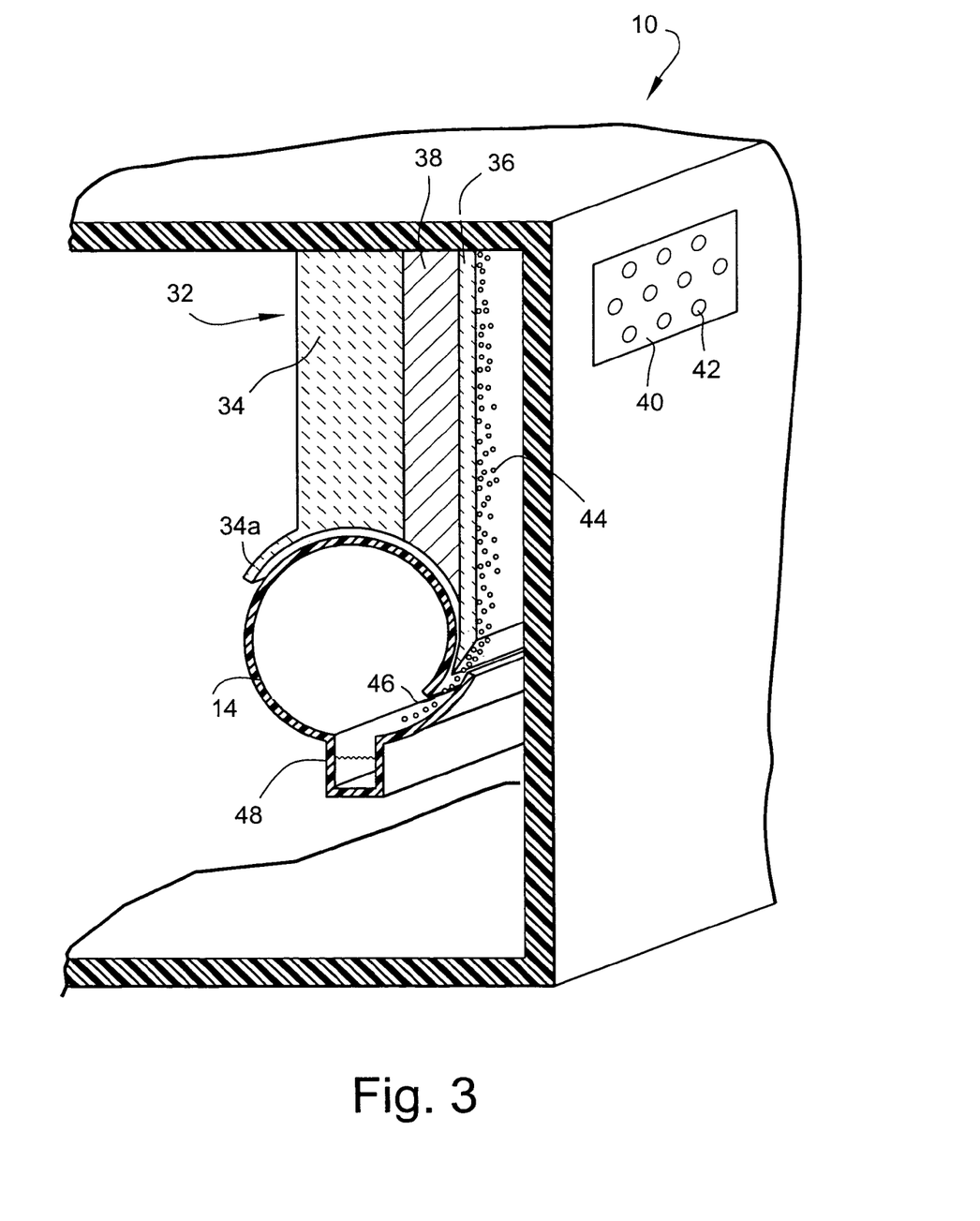
FIG. 3 is a schematic, cross-sectional, perspective view along line 3-3 of FIG. 1.

FIG. 3 is a perspective, schematic and partial cross-sectional view of blower 10 in which Peltier plate 32 is provided within blower casing. Blower casing may include at least one vent 40 having one or more openings 42. In this example, heat is transferred from ceramic layer 36 to ceramic layer 34 such that ceramic layer 36, which is provided adjacent vent 40, begins to collect water droplets 44. Droplets 44 descend by gravity along the surface of ceramic layer 36 and are deposited into an opening 46 provided in internal conduit 14. Layer 36 may also be a porous medium that increases the surface area. Some or all of the air may be passed along the surface to increase humidification. Internal conduit 14 may include a reservoir 48 to collect accumulated droplets once they are received with opening 46. A level detector may be provided to determine whether the level with receptacle 48 reaches a predetermined maximum limit, at which point the Peltier plate 32 would be switched off or reduced in order to cease production of water droplets and condensation.

Figures 4, 4A, 4B:
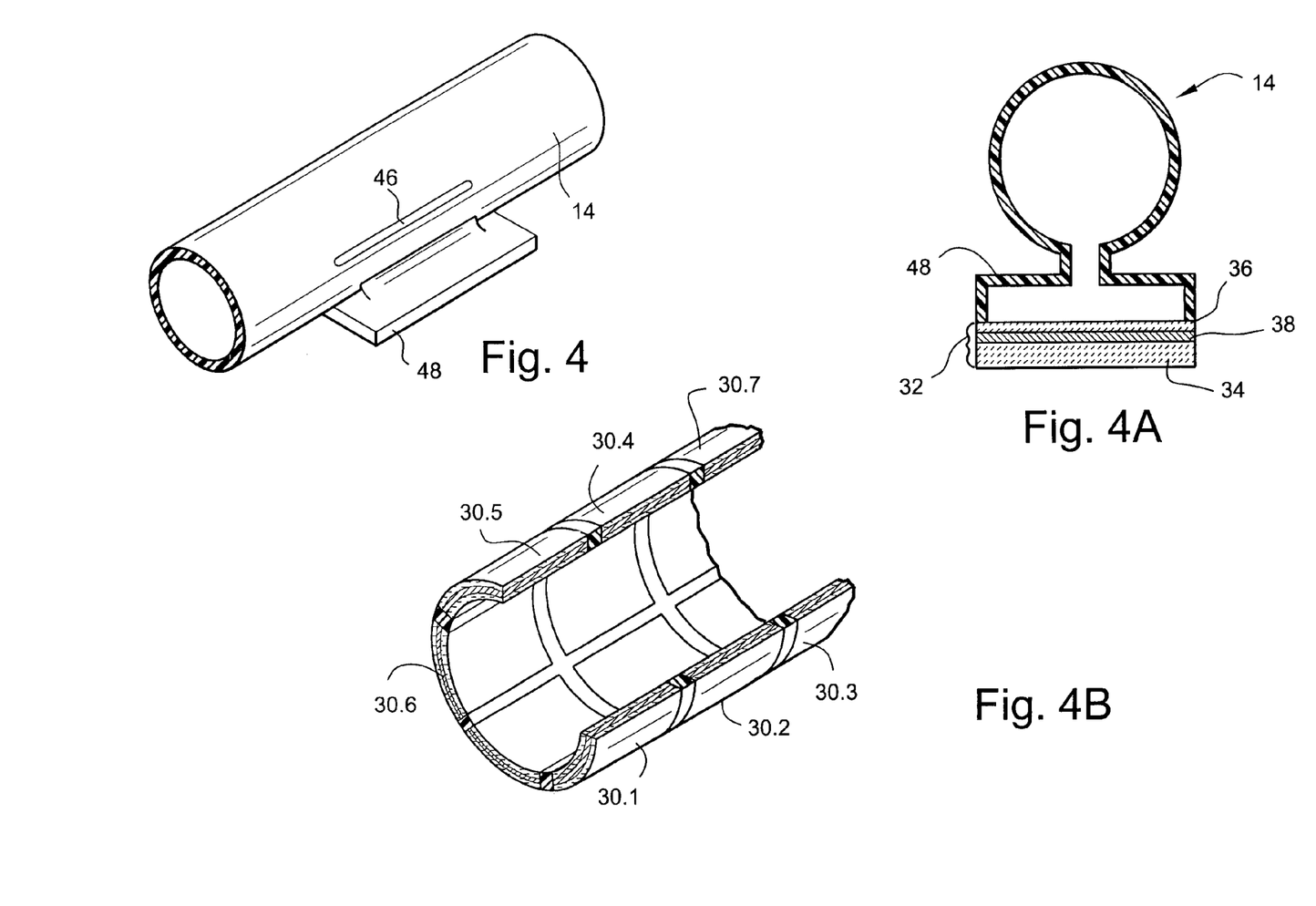
FIG. 4 is a perspective view of an alternative internal conduit according to an embodiment of the present invention.
FIGS. 4A-4B are schematic cross-sectional views of internal conduits according to alternative embodiments of the present invention.

FIG. 4 illustrates an isometric view showing a portion of internal conduit 14 along with reservoir 48. As shown, reservoir 48 extends along only a portion of the extent of conduit 14. However, the length of reservoir can be changed depending on the desired condensation capacity and/or the size of the Peltier plate 32. Moreover, the length of conduit 14 can be changed to allow for an increase or decrease in the size of the reservoir and/or the size of the Peltier plate. In one embodiment, the conduit 14 may have a series of bends (with respective reservoirs or a common reservoir) to effectively increase the length. The reservoir may have a capacity that is very small or negligible, e.g., 10-20 mL or less. If this volume is spread over a sufficiently large surface area, which is preferably very shallow or film-like, it can be heated from water or liquid to gas vapor prior to introduction to breathing gas.

FIG. 4A is a schematic cross-sectional view according to another embodiment of the present invention. In FIG. 4A, conduit 14 includes a Peltier plate 32 provided to the bottom of reservoir 48. Layer 36 forms a lower surface of the reservoir 48. The polarity of the current introduced into plate 32 can be reversed, such that plate 36 can either produce condensation, to add humidification, or heat the reservoir 48, to heat the air and/or evaporate any collected condensation. In one embodiment, controller 24 (FIG. 1) can cycle plate 32 to eliminate any collected moisture/water in reservoir at the end of a treatment session, e.g., by using layer 36 in a heating mode to convert the water into gas vapor that may be reintroduced in the breathing gas as humidified air/gas. In addition, controller 24 can cycle plate 32 to begin production of water or moisture at some predetermined time before the treatment session begins.

In yet another embodiment, the conduit need not include a reservoir, if the amount of water/moisture/condensation produced is approximately equal to the amount of humidity to be added to the air flow path. In one example shown in FIG. 4B, the conduit 14 may be provided with a plurality of axially and/or circumferentially spaced humidification units 30.1-30.7 that can be individually controlled to produce the desired humidification without the need to collect water or provide a reservoir.

For Peltier plates to function efficiently, the 'waste' heat needs to be removed from the hot side. In the application of a patient ventilation device, the heat could be removed by the incoming breathable gas, which may improve comfort of breathing especially in cooler climates. As shown in FIG. 3, "hot" ceramic layer 34 may be in close proximity to the outer surface of internal conduit 14 to heat the pressurized gas. Layer 34 may include an extension 34a to heat a further extent of conduit 14, if desired. Extension 34a may be independently operable, to thereby change the temperature of the heated gas.

The 'waste' heat may also be partly or fully utilized to re-evaporate the condensed water from the cool side of the Peltier plate. The evaporation of the liquid water into water vapor therefore provides a method of humidification for the breathable gas.

In another embodiment, the cool side may only be exposed to the ambient air outside of the breathable gas air path. This prevents the breathable gas from being cooled if so desired. In the case of ventilation, warmer breathing air is more comfortable to the airways. The hotter side of the Peltier plate may be exposed to the breathable gas path so as to heat the breathing gas. The water condensed from the cool side can then be transferred or otherwise run-off onto the hot side in the breathable gas path, which results in the breathable gas being heated and humidified. The system would allow only heating, or heating and humidification.

In this application of the Peltier technology, the moisture from condensation is insulated from the core of the Peltier plate, as moisture will have an adverse effect on the life.

A Peltier plate is currently the preferred embodiment of the invention due to no noise, no vibration, no moving parts, long life, no Freon™-type refrigerant, compact size, and capable of precision temperature control.

Two or more Peltier plates may also be stacked upon one another to achieve higher performance; that is greater cooling and/or heating. For example, a second metal layer similar to layer 38 could be provided to the left side of layer 34 in FIG. 3, and an additional ceramic layer provided to the second metal layer.

Figures 5, 6:
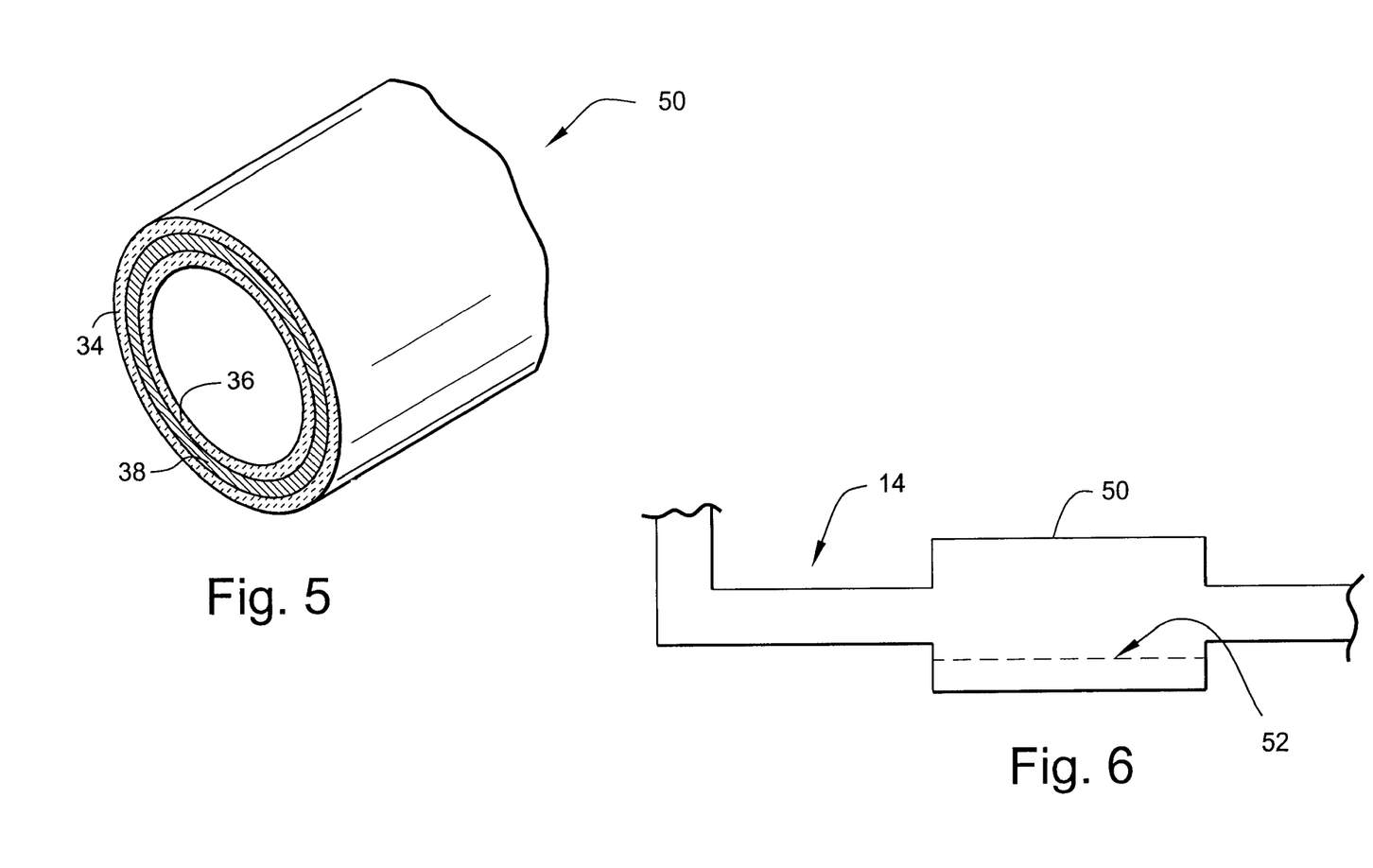
FIG. 5 is a partial perspective and cross-sectional view of a portion of an internal conduit according to still another embodiment of the present invention.
FIG. 6 is a schematic view including the internal conduit portion of FIG. 5.

FIG. 5 illustrates a Peltier plate assembly according to yet another embodiment of the present invention. In FIG. 5, Peltier plate assembly takes the form of a conduit including ceramic layers 34 and 36 and metal layer 38. Conduit 50 may form at least a portion of internal conduit 14, as shown in FIG. 6. As shown in FIG. 6, Peltier plate assembly 50 has a diameter which is larger than the diameter of the remainder of internal conduit 14. Accordingly, the water level 52 which is shown in dotted lines in FIG. 6 can be maintained below the level of conduit 14, so as to maintain the condensed moisture within conduit portion 50.

Figure 7:
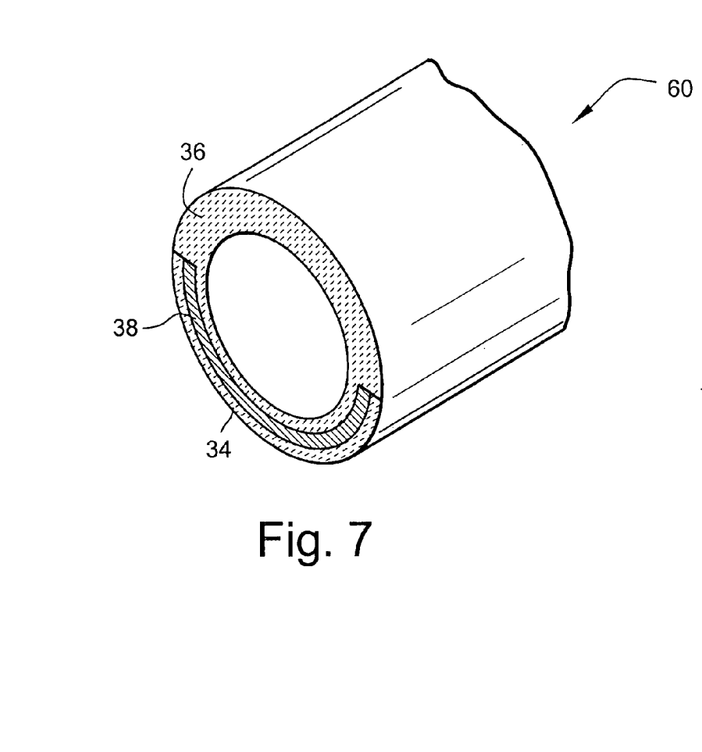
FIG. 7 is a partial perspective and cross-sectional view of a portion of an internal conduit according to another embodiment of the present invention.
Figure 8:
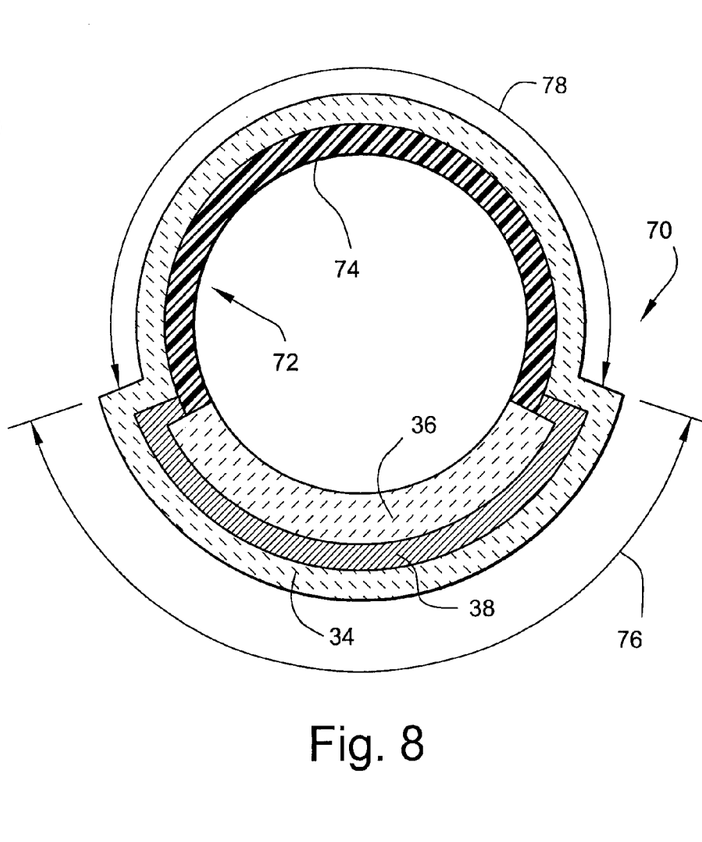
FIG. 8 is a schematic, cross-sectional view of an internal conduit according to still another embodiment of the present invention.

FIGS. 7 and 8 illustrate further Peltier plate assemblies according to the present invention. As shown in FIG. 7, conduit portion 60 is formed such that ceramic layer 34 only covers a portion of the circumference of conduit 60. The conduit per se in FIGS. 5 and 7, which is used to convey pressure as gas and store condensed fluid, may be formed of a ceramic material. Alternatively, a standard plastic conduit may be inserted within conduit portion 60. Stated differently, the conduit portion 60 could form a sleeve that could be retrofit onto a portion of a conduit of a prior art blower.

In FIG. 8, conduit member 70 includes an inner surface 72 which is partially defined by plastic portion 74 and partially defined by ceramic layer 36. Metal layer 38 is provided between ceramic layers 34, 36. When a DC current is applied, heat may be transferred from layer 36 to layer 34, which produces condensation on layer 36, in order to humidify the air. In addition, layer 34 is in contact with plastic portion 74 so as to allow the possibility of heating the air to a desired temperature level. As schematically illustrated in FIG. 8, the lower portion 76 of layer 34 may be controlled independently of the upper layer 78 of layer 34, so as to control the humidity level independently of the heating level.

The Peltier plate, in any embodiment described herein, may also have reversible current to potentially cool air that has become too hot or otherwise to control level of humidity. In the case of humidity, the Peltier plate may re-condense the humidified breathable gas if humidification levels were deemed too high.

The Peltier system (or any system described herein) may also have variable current that allows the level of humidification to be variable or have multiple phasing in/out so that humidification may be profiled according to requirements. Attention is directed to U.S. Provisional Patent Application No. 60/599,864, filed on Aug. 10, 2004, entitled "Method and Apparatus for Humidification of Breathable Gas With Profiled Delivery," incorporated herein by reference in its entirety.

It can be observed that water can condense on a cool surface especially when the cool surface is brought into a warmer environment. Another embodiment of the invention is known as a pulsed Peltier effect. It has the ability to quickly create condensation on the surface of the cool side of the Peltier plate. Should the DC current to the Peltier plate be reversed, to now warm the same surface, this can encourage faster condensation should the treatment system require it.

Refrigeration Methods

Figure 9:
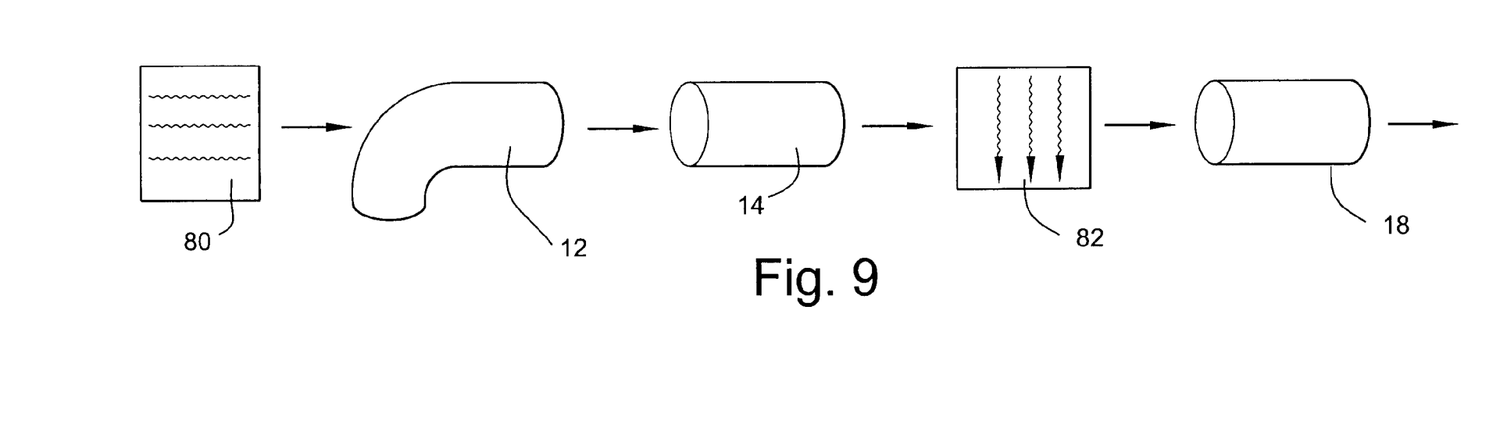
FIG. 9 is a schematic view of a process for use of refrigeration to produce condensation for use with a blower, according to another embodiment of the present invention.

Refrigeration systems evaporate fluorocarbons such as Freon™, e.g., using a hot coil (condenser coils) and a cold coil (evaporator coils). The cold coil condenses the water whilst the hot coil is exposed to breathing gas to warm air for comfort. The condensed water from the cold side is introduced into the warm breathing gas or hot coil side. As shown in the example of FIG. 9, a hot coil 80 is provided to the inlet of blower motor 12, which then provides the gas to conduit 14. Conduit 14 is in communication to receive condensation from cold coil 82, which allows humidified gas to be provided to the patient via tube 18. The systems range in size with compressors about the size of a soccer ball in a typical domestic fridge to miniature sizes approximately fits the palm of one's hand. The miniature refrigeration systems have been used in armed forces apparel in arid conditions where the system is used to cool the wearer.

Miniature refrigeration systems are well known devices, for example for cooling food. These refrigeration systems re-evaporate the condensed water that is considered waste. In the case of the invention, the water is collected for processing and subsequently used in humidification of a breathing gas.

The same embodiments mentioned under "Peltier Methods" (above) may also be applied to refrigeration as it also has a combination of a hot surface and cold surface, more specifically a hot coil and cold coil.

The refrigeration pump may use "Inverter" type technology where the speed of the pump can be varied to control cooling/heating efficiency, rather than switching on and off to control output/temperature.

The refrigeration pump, like the Peltier technology can be reverse-cycle (change-over), where the heating coil becomes the cold one and the cooling coil becomes the hot one.

Those embodiments of the invention that have cold and hot elements in the same system (Refrigeration and Peltier) can also condense the moisture from the cold coil and the dehumidified air may be passed back through to offer greater comfort of warm breathing air. The level of humidification may be adjusted manually, semi, or fully automated by modifying the level of moisture being re-evaporated or vaporized into the breathing gas.

Freezer Pack Embodiments

Figure 10:
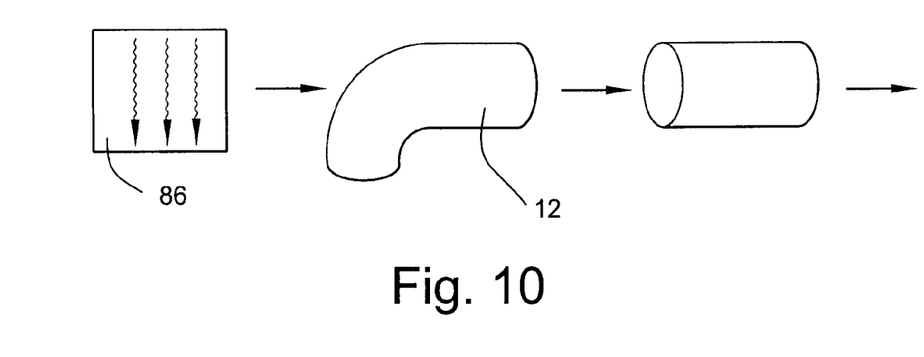
FIG. 10 is a schematic view of a process for use of a freezer pack to produce condensation for use with a blower, according to yet another embodiment of the present invention.

Another embodiment includes the use of a freezer pack. The pack could eliminate need to clean or replenish a reservoir. An ice pack, powder, gel, or other method of storing cold or frozen material may be used. The freezer pack in one aspect may be frozen in the fridge then taken out and placed into the treatment device. The condensation from the freezer pack is subsequently heated and re-evaporated before administering into the breathable gas. If so desired, the device may not reheat the air, but simply pass the ambient air over the condensation-covered ice pack to raise humidity and cool the air, possibly desirable in hot climates. This is schematically illustrated in FIG. 10, in which freezer pack 86 is provided upstream of blower motor 12. Of course, freezer pack may be provided along any portion of the air delivery path.

Figure 11:
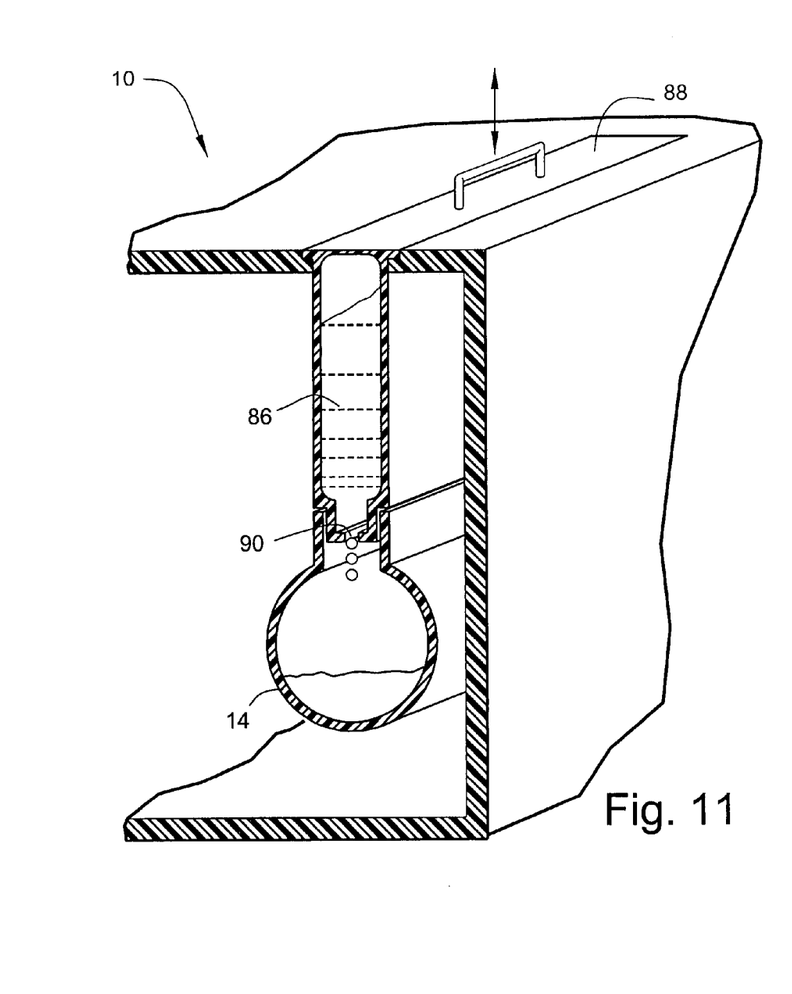
FIG. 11 is a schematic perspective view of a removable drawer for a blower according to still another embodiment of the present invention.

The freezer pack, in a preferred embodiment, is a sealed bag or bladder that can conveniently contain the cold packing material, e.g., water. The bag may be in a shape that occupies a desired space with the most compact dimensions. As shown in FIG. 11, freezer pack 86 may be delivered/removed using an insert member 88, e.g., a slidable drawer or shelf, that can be removed or slid open to expose the inside of blower 10. Insert member 88 includes an opening 90 in communication with an opening in conduit 14 to allow for collected moisture to be delivered to conduit 14.

The freezer pack may also be used in conjunction with any form of device that may elevate the surrounding temperature (of the freezer pack) to increase the rate of condensation. An example of this is taking a can of cold drink out of the fridge and placing it in a warm room. The sides of the can exhibit dripping moisture as condensation.

The water collected may either be directly humidified or otherwise end up in a reservoir for subsequent use, for example conventional heated humidification.

Cold material may also be contained in a holding body without the use of a bag, bladder or wrapper. For example, it may be in the form of cold storage medium that is semi-solid liquid or gel, similar to cold packs used in cosmetics around the eyes.

The material that may be cooled could include any or a combination of liquid, gas, powder, granule, fluid, viscous fluid such as gel, solid particles or a solid that is a pre-shaped mass.

Other Embodiments

In the case of CPAP therapy where the flow generator device is generally only used at night-time, the device according to the invention may be designed to be relatively low in power and less efficient than other embodiments mentioned (and potentially smaller capacity and size requirements). For example, it may collect about 0.5 liters of water into a reservoir over a period of say 10-15 hours (sleep is around 8 hours). Another embodiment of the invention allows the device to collect water from the atmosphere during the daytime while the patient is not being treated, and by night-time, the device has accumulated enough condensed water in a reservoir (essentially a self-filling reservoir), and therefore behave like conventional humidifier systems (with a reservoir and heating plate) at the time CPAP therapy begins. It may have an automated switch off device once the reservoir is filled to maximum.

With reference to the embodiment above, the device may also be a combination of a low power heat pump and a reservoir that is heated. This allows the unit to switch from heat pump to humidification-efficient heated reservoir as required by the patient. In this scenario, the reservoir size may be substantially reduced in size. The switchover between modes may be incremental and concurrent, otherwise may completely switch completely from one to the other.

The unit may have an additional reservoir of water to compensate for dryer periods during a treatment session and also be used to assist with cooling the hot side of coil (refrigeration or Peltier) for greater cooling efficiency. The small reservoir may also provide an additional humidification source if insufficient moisture is temporarily unavailable in the atmosphere.

The device may only condense water but not heat (similar to passive or Passover humidifiers). Humid cool air is perceived warmer and more comfortable than dry cool air. The dry cool air tends to cool more because there is a higher rate of evaporation. This option may be desirable where only relatively small levels of humidification are required.

Water may move over mesh device to increase surface contact with air to improve efficiency moisture take-up of the air.

Device may be located at the inlet of the gas delivery device (CPAP) or between the gas delivery device and the patient interface.

Device may utilize a typical air conditioner used to cool or heat the room. The drain for the air conditioner's condensate may also be connected to the humidifying device that introduces the moisture to the breathing air.

An anti-microbial filter or other barrier may be incorporated into the system to prevent bacteria in the moist paths from entering the breathable gas.

The invention may also be used with or without a ventilator device, may be a stand-alone unit to administer vaporized gas.

The invention in one preferred embodiment may cycle between switch on and off during the course of the night. These cycles can be regular, irregular, or otherwise controlled for numerous intervals and various durations using some smart electronic control. The switching off does not necessarily need to completely switch off, but may reduce in temperature during periods where less humidification is required. As mentioned, this reduces water usage.

The device (invention) may also measure room temperature, humidity or both as well as monitoring the breathing gas to be delivered to the patient and optimize setting to produce a desired humidification profile. For example, constant level or variable over the course of the treatment session (night). These sensors may be integral with the device or otherwise remote with wired and/or wireless "Blue tooth" communication.

Freezing Gas

Figure 12:
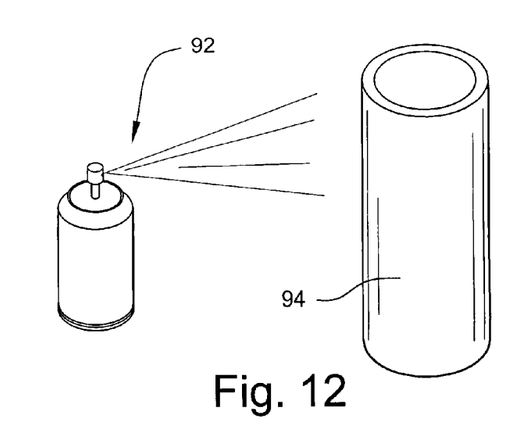
FIG. 12 is a schematic view of a coating, e.g., a spray coating, for use in producing condensation, according to yet another embodiment of the present invention.

A freezing gas may also be used to reduce the temperature of the air below the Dew Point. For example, as shown in FIG. 12, a freezing aerosol 92 may be sprayed onto a surface, e.g., a conduit 94 forming part of the air delivery path, in contact with ambient air. Freezing aerosols are commonly used in electronics had traditionally been halogenated CFC (Chlorofluorocarbon). More environmentally friendly substances can now be used, such as Hydrofluorocarbons HFC 134a and HFC 152a. These gases are also used in refrigeration systems quoted above. Any freezing gas that can reduce the air below its Dew Point may be used. For example, Liquid Nitrogen.

Phase Change Materials

A phase change material (PCM) may also be used in further embodiments. PCMs can be described as materials that can change in physical form. For example, from solid to liquid, and from liquid to gas as temperature changes.

During a phase change from solid to liquid and liquid to gas, heat is absorbed from the surrounding environment. An example is paraffin wax. Conversely, in cooling from a gas to liquid and liquid to solid, heat can be given off to the environment. The energy that can be stored or released is known as latent heat, and in PCM, occurs over a narrow range of temperature. During the change in physical state, the material tends to remain at relatively constant temperature until phase change is complete. The transfer of the latent heat to surroundings produces a broad plateau of near constant temperature.

An embodiment includes the use of a PCM to cool a surface. Furthermore, the near constant temperature characteristics explained earlier, may be utilized with any other form of cooling or heating process to assist in maintaining temperatures with less fluctuations. This in turn may provide more constant temperature control if so desired. For example, a PCM may be used in conjunction with the refrigeration example explained earlier.

The PCM may be in many forms. Paraffin wax is one example. It may also be in the form of eutectic salts or otherwise be in a number of forms including liquid, gel, powder, paste or granule, or blended into part of another solid. For example placing granules into a thermosetting material.

Moisture Absorbent Materials

Further embodiments to the invention may also use moisture absorbent materials such as Silica Gel, typically found in crystalline form. This substance is widely used to absorb atmospheric moisture. The moisture or water vapor trapped in these crystals may subsequently be harnessed to re-vaporize into the breathing gas, for example by heating.

Silica Gel is one substance that absorbs atmospheric moisture relatively efficiently. The invention is not limited to the type of substance used and in general terms, this embodiment relies on the use of a desiccant material. Silica Gel is basically a substance with millions of tiny pores that can trap moisture.

Desiccants

A further embodiment uses the desiccant to control the level of condensation that occurs. For example, excessive condensation may be controlled by using Silica gel to absorb some of the excess moisture.

Figure 13:
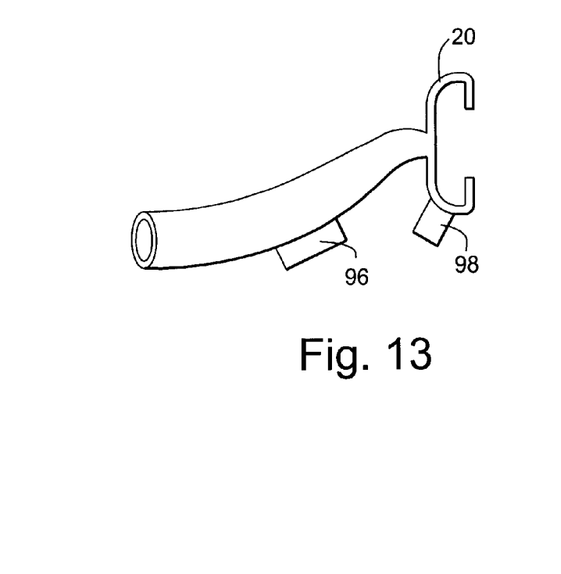
FIG. 13 is a schematic view of an air delivery tube and patient interface equipped with a desiccant unit for removal of moisture or water, according to another embodiment of the present invention.

For example, as shown in FIG. 13, a desiccant unit 96 (including a desiccant) may also be applied to the breathing tube 18 to assist in prevention of water droplets in the tube. Desiccant can alternatively be provided within a unit 98 provided on patient interface 20. This condensation in the breathing tube can cause irritation if a patient inadvertently inhales it.

Embodiments of the invention may also incorporate a switch or sensor device that switches off the humidifier should the treatment session be interrupted. For example, an OSA patient may get up in the middle of the night to go to the bathroom. This feature is designed to reduce water consumption further and also prevent condensation in the air delivery pipe, especially if the flow generator has stopped. The flow generator can be stopped or started by sensing flow/pressure in the air path, e.g., when the patient dons or removes the mask, to thereby create a signal to activate or deactivate the blower. Such technology is incorporated, e.g., in ResMed's Smartstart™ with smart stop and/or smart start feature. It may also prevent the patient breathing in condensate when they return to bed, which in turn improves patient comfort.

Condensation Moisture Sensor

Figure 14:
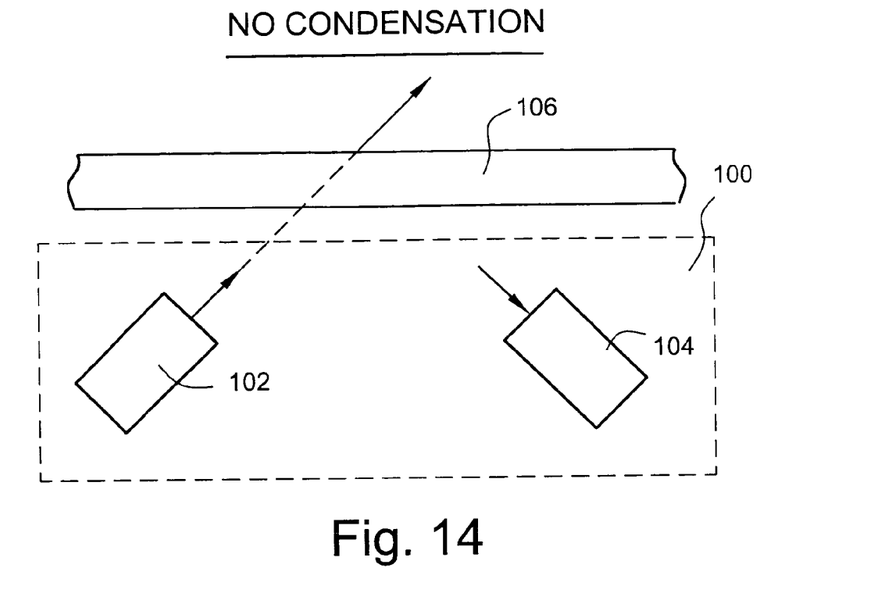
FIGS. 14 and 15 are schematic views of a sensor arrangement according to an embodiment of the present invention.
Figure 15:
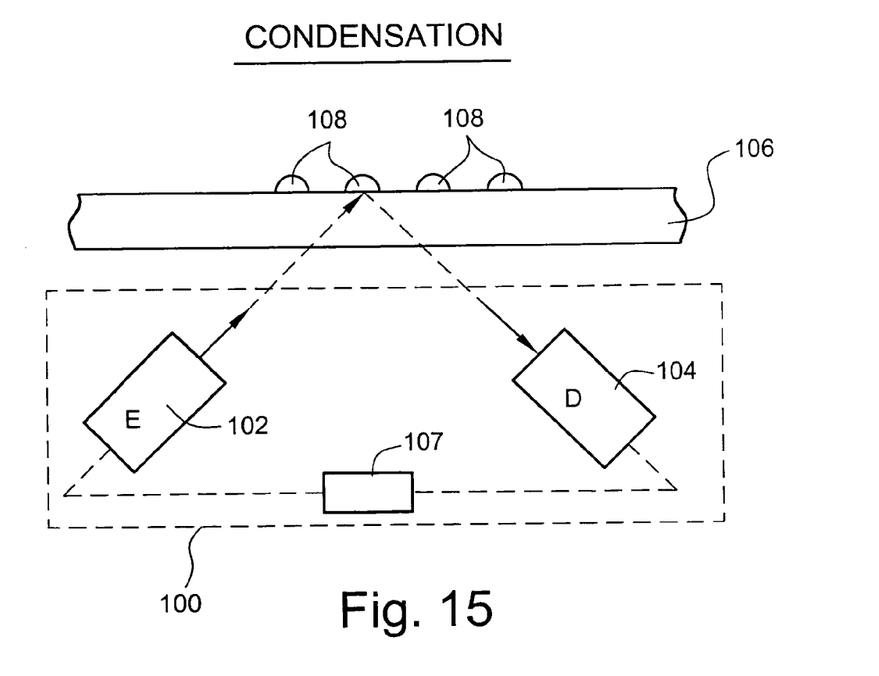

As shown in FIGS. 14 and 15, one embodiment of the invention may include a humidity or condensation sensor 100 to determine if adequate level of condensation, or too much condensation, is occurring. A mask "rain-out" sensor according to an embodiment does not require the use of humidity sensor like the prior art. As schematically shown in FIG. 14, an infrared emitter 102 and detector 104 are placed, e.g., in side-by-side relation, at the bottom of the mask interface or location or surface 106 where condensation is likely to bead or pool. The mask frame wall in front of the side-by-side emitter/detector is transparent to infrared light. Under normal conditions, where no condensation or water droplets have developed (FIG. 14), the detector 104 does not detect any infrared light. If significant water droplets 108 develop in front of the emitter/detector (FIG. 15), the droplets (condensation) cause the incident light to scatter in most if not all directions, a portion of which scattered light is reflected back to the detector to thereby signify the presence of condensation. Sensor elements, e.g., emitter and detector, are controlled by appropriate logic, or signals from the detector/emitter are provided to a processor or computer. The sensor may also use another type of visible or non-visible light emitter/detector combination.

In another alternative, emitter and detector may be positioned on opposite sides of the location 106. If the light from emitter passes through location 106, and is received by detector 104 at full intensity, then it is judged that no condensation is present. If water droplets (condensation) appears, then the emitted light is reflected and/or scattered such that the detector only receives less than the full intensity of the light, e.g., 50-95%. Therefore, it is judged that condensation is present.

A controller 107 associated with the detector would preferably be calibrated or set such that it can distinguish between full intensity light (no condensation) and less than full intensity light (condensation). The controller may produce a positive or negative condensation signal depending on whether the detector produces a sensed light intensity signal that is equal to or greater than a predetermined full intensity signal. The sensed intensity of the light changes depending on whether condensation is causing the light to reflect/scatter.

The emitter/detector above may also be used to sense the level of liquid where a reservoir is used.

The above described embodiments may realize one or more of the following advantages:

- A humidifier that does not need to be manually filled with water by a user.
- Because there is a smaller reservoir or no reservoir, there is less spilt water.
- Because the humidification unit is self-initiating, there is not need for continuous top ups.
- Water volume requires no consideration. Only requirement is to set humidification level required.
- Major benefit over current technologies that does not require a user to manually fill a reservoir.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability to ventilators in general for use with patients and non-patients alike.

The invention claimed is:

1. A condensation sensor arranged to detect condensation, said sensor comprising:
    an emitter to emit light towards a location in a mask system or positive airway pressure (PAP) device where condensation is likely to beed or pool; and
    a detector structured to receive the emitted light in dependence on the condensation present at the location.

2. The condensation sensor according to claim 1, wherein the emitter and the detector are positioned on a common side of the location, such that the emitted light is reflected from a surface of the location towards the detector if condensation is present.

3. The condensation sensor according to claim 1, wherein the emitter and the detector are positioned on opposite sides of the location, such that the emitted light passes through a surface of the location towards the detector at substantially full intensity if no condensation is present.

4. The condensation sensor according to claim 3, wherein only a portion of the emitted light passes through the surface towards the detector if condensation is present.

5. The condensation sensor according to claim 3, further comprising a controller that receives a light intensity signal from the detector, wherein the controller produces a negative condensation signal if the light intensity signal is equal to or greater than a predetermined full intensity signal, and the controller produces a positive condensation signal if the light intensity signal is less than the predetermined full intensity signal.

6. The condensation sensor according to claim 1, wherein the location is proximate to a bottom of a patient interface of the mask system.

7. The condensation sensor according to claim 1, further comprising a processor configured to determine an amount of condensation proximate to the location.

8. The condensation sensor according to claim 7, wherein the processor is further configured to determine whether the amount of condensation proximate to the location is a therapeutically adequate level of condensation.

9. The condensation sensor according to claim 1, wherein the emitted light is infrared light.

10. A method of detecting condensation, the method comprising:
    emitting light towards a location in a mask system or positive airway pressure (PAP) device where condensation is likely to beed or pool via an emitter; and
    receiving, via a detector, emitted light emitted via the emitter in dependence on the condensation present at the location.

11. The method according to claim 10, further comprising positioning the emitter and the detector on a common side of the location, such that the emitted light is reflected from a surface of the location towards the detector if condensation is present.

12. The method according to claim 10, further comprising positioning the emitter and the detector on opposite sides of the location, such that the emitted light passes through a surface of the location towards the detector at substantially full intensity if no condensation is present.

13. The method according to claim 12, wherein only a portion of the emitted light passes through the surface towards the detector if condensation is present.

14. The method according to claim 12, further comprising providing a controller arranged to receive a light intensity signal from the detector, wherein the controller is configured to produce a negative condensation signal when the light intensity signal is equal to or greater than a predetermined full intensity signal, and wherein the controller is configured to produce a positive condensation signal if the light intensity signal is less than the predetermined full intensity signal.

15. The method according to claim 10, wherein the location is proximate to a bottom of a patient interface of the mask system.

16. The method according to claim 10, further comprising determining an amount of condensation proximate to the location.

17. The method according to claim 16, further comprising determining whether the amount of condensation proximate to the location is a therapeutically adequate level of condensation.

18. The method according to claim 10, wherein the emitted light is infrared light.

19. A respiratory assistance apparatus, comprising:
    a mask;
    a flow generator; and
    a condensation sensor according to claim 1.

* * * * *